United States Patent
Choukroun et al.

(10) Patent No.: US 10,201,273 B2
(45) Date of Patent: Feb. 12, 2019

(54) METHOD FOR DETERMINING OCULAR MEASUREMENTS USING A CONSUMER SENSOR

(71) Applicant: FITTINGBOX, Labege (FR)

(72) Inventors: Ariel Choukroun, Toulouse (FR); Sylvain Le Gallou, Baziege (FR)

(73) Assignee: FITTINGBOX, Labege (FR)

( * ) Notice: Subject to any disclaimer, the term of this patent is extended or adjusted under 35 U.S.C. 154(b) by 0 days.

(21) Appl. No.: 14/903,540

(22) PCT Filed: Jul. 16, 2014

(86) PCT No.: PCT/EP2014/065266
§ 371 (c)(1),
(2) Date: Jan. 7, 2016

(87) PCT Pub. No.: WO2015/007784
PCT Pub. Date: Jan. 22, 2015

(65) Prior Publication Data
US 2016/0166145 A1     Jun. 16, 2016

(30) Foreign Application Priority Data

Jul. 16, 2013   (FR) .................................... 13 56990

(51) Int. Cl.
*A61B 3/00*     (2006.01)
*A61B 3/10*     (2006.01)
(Continued)

(52) U.S. Cl.
CPC ............ *A61B 3/111* (2013.01); *A61B 3/0041* (2013.01); *A61B 3/14* (2013.01); *A61B 3/145* (2013.01)

(58) Field of Classification Search
CPC ......... A61B 3/111; A61B 3/0041; A61B 3/14; A61B 3/145; A61B 3/11; A61B 3/0058;
(Continued)

(56) References Cited

U.S. PATENT DOCUMENTS

2010/0220285 A1* 9/2010 Simmonds ........... G02C 13/005
351/204
2011/0267578 A1* 11/2011 Wilson ................... A61B 3/111
351/204
(Continued)

FOREIGN PATENT DOCUMENTS

DE      102 07 316 A1    9/2003
DE      10207316    *    11/2003    ............... A61B 3/11
(Continued)

OTHER PUBLICATIONS

International Search Report, dated Oct. 23, 2014, from corresponding PCT Application.

*Primary Examiner* — Mustak Choudhury
(74) *Attorney, Agent, or Firm* — IM IP Law; C. Andrew Im; Chai Im

(57) ABSTRACT

Disclosed is a method for determining at least one ocular measurement (pupillary distance, mono pupillary distance and/or heights) of a user, using a consumer-type digital image sensor. The method uses at least one image of the user's head, acquired by the image sensor and containing an object of known size. The calibration parameters of the camera are unknown or known with little precision.

20 Claims, 2 Drawing Sheets

(51) Int. Cl.
    *A61B 3/11*        (2006.01)
    *A61B 3/14*        (2006.01)
(58) Field of Classification Search
    CPC ..... A61B 3/113; A61B 5/0002; A61B 3/0025;
            A61B 3/10; A61B 3/103; G02C 13/005;
            G02C 13/003; G06T 7/60; G06T 19/20;
            G06T 17/00; G06K 9/00604; H04N
            13/0484; G01B 11/02; G09G 5/00
    USPC ......... 351/246, 204–206, 209, 211; 345/420,
                   345/629, 632, 633, 661; 356/124;
                                                 348/78
    See application file for complete search history.

(56)            References Cited

U.S. PATENT DOCUMENTS

| 2013/0076884 | A1  | 3/2013  | Choukroun    |           |
|--------------|-----|---------|--------------|-----------|
| 2013/0107207 | A1* | 5/2013  | Zhao ........ | A61B 3/0058 |
|              |     |         |              | 351/206   |
| 2013/0141468 | A1* | 6/2013  | Coon ........ | G09G 5/00 |
|              |     |         |              | 345/661   |
| 2013/0314413 | A1* | 11/2013 | Coon ........ | A61B 3/111 |
|              |     |         |              | 345/420   |
| 2014/0152956 | A1  | 6/2014  | Silva et al. |           |
| 2014/0253875 | A1  | 9/2014  | Le Gallou et al. |       |

FOREIGN PATENT DOCUMENTS

| EP | 1 728 467   A1 | 6/2006 |
| FR |    1052001  A  | 1/1954 |
| WO | 2011/113936 A1 | 9/2011 |
| WO | 2013/045531 A1 | 4/2013 |

* cited by examiner

METHOD FOR DETERMINING OCULAR MEASUREMENTS USING A CONSUMER SENSOR

FIELD OF THE INVENTION

The invention relates to the field of optics. It more particularly relates to the field of manufacture of lenses for correcting vision.

PRIOR ART

In the context of the manufacture and fitting of corrective spectacle lenses, it is necessary to know with the highest possible precision ocular measurements such as interpupillary distance, monocular pupillary distance and pupillary heights.

Interpupillary distance (denoted PD in the rest of the description) is the distance between the centers of the pupils when the subject looks to infinity.

Monocular pupillary distance (denoted MonoPD in the rest of the description) is the distance between the projection of the pupil onto the plane of the lens and the center of the frame. This quantity measures the horizontal shift to be applied during the edging of the lens.

Pupillary height is the distance between the projection of the pupils onto the plane of the lens and the bottom of the frame (presumed interior of the internal bezel). This quantity measures the vertical shift to be applied during the edging of the lens.

SUMMARY OF THE INVENTION

The invention consists in determining optical and ocular measurements enabling manufacture and precise fitting of corrective lenses in a pair of spectacles from an image.

The advantage of the present method is that it guarantees a precise and reliable measurement even if the cameras are cameras of large field aperture, such as webcams or mobile cameras, and the quality of the images is not good: low resolution and high image compression. Other methods for their part work in theory but do not guarantee the required precision in practice.

This patent application is an extension of the 3D analysis proposed in patent FR 10 52001, to measurements from a single image. The method described here guarantees a precision of 0.5 mm, achievable with commercially available cameras, even if they are of poor quality. It is applicable, in an 'Internet' context, at home, using everyday tools, and in an opticians. Solutions that would appear obvious to those skilled in the art are analyzed and their theoretical and practical invalidity is explained.

Contrary to the prior art, we propose ocular measurement solutions that are implementable without expertise with mass-market sensors (and therefore in any context) and that do not require a complex gauge to be used. The gauge will possibly either be an object of known size that the user has to hand (a credit card for example) or even his own face in 3D, reconstructed metrically. We also propose a particular protocol that does not require there to be any gauge in the scene.

Thus, the invention relates, according to a first aspect, to a method for determining at least one ocular measurement (interpupillary distance, monocular pupillary distance and/or pupillary heights) of a user using a mass-market digital image sensor. The method uses at least one image of the head of the user, acquired by the image sensor, containing an object of known size, and the calibration parameters of the camera are unknown or known with little precision.

It is possible to obtain a measurement with a single image acquisition, or a plurality, contrary to prior methods that were erroneous with a single image, or that required a substantial number of images to provide a reliable solution.

In embodiments:
the object of known size is the face of the user.
the object of known size is a flat object.
the object of known size is a pair of spectacles.

In one particular embodiment, the head of the user is placed face-on in at least one image.

In one particular embodiment, the user is at a known distance from the acquiring device and the object of known size is positioned at a known distance from the zone forming the subject of the ocular measurement.

In one particular embodiment, the user is guided by an interactive system for helping with correct positioning.

In one particular embodiment, the interactive system for helping with correct positioning is a shape drawn on the display screen (a face shape for example).

In one particular embodiment, the interactive system for helping with correct positioning includes recommendations derived from real-time tracking of the face of the user.

In embodiments:
the image sensor is calibrated and acquires images while moving around the face of the user who looks at a point at infinity.
the image sensor is calibrated and acquires images while moving around the face of the user who looks at points displayed on a screen.
the image sensor is calibrated and delivers a depth map of the scene. The image sensor is then for example a sensor such as the Kinect (registered trademark).

BRIEF DESCRIPTION OF THE FIGURES

The aims and advantages of the invention will be better understood on reading the description and from the drawings of one particular embodiment, given by way of nonlimiting example, and for which the drawings show.

DETAILED DESCRIPTION OF ONE EMBODIMENT OF THE INVENTION

Scaling and Existing Systems: Analysis

In order to obtain the measurement of a particular quantity (PD, monoPD, height) from one image, we propose to carry out scaling. Specifically, knowing the actual size of an object present in the image, it is possible to obtain an estimation of the actual size of the desired quantity by comparing their size in pixels in the image. Contrary to existing systems not placing constraints on the gaze of the subject and on the way in which the gauge object is positioned, our method allows the scaling to be used optimally, by controlling measurement precision.

Specifically, all the proposed protocols are subject to parallax and scaling errors induced by the distance between the reference object and the object to be measured (namely the ocular distance measurements) and the orientation of the planes containing the reference objects and object to be measured. Although in theory it is possible to scale two objects in an image, the precision required for the ocular measurements is never guaranteed when a protocol is actually carried out, because of theoretical and practical constraints that are not met.

We list here reasons for error in measurements obtained from a single image and with any given camera. These errors are commonly made in all existing techniques for scaling measurements from a known object.

As regards the generation protocol, we consider that the user positions a planar gauge (object of known size) by pressing it against his face, centered on his eyes, i.e. on his mouth or on his forehead, in order to form a rigid face/gauge system.

In the case of a still image (derived from a photograph, video or real-time stream), we consider the intrinsic parameters of the camera to be unknown. If we consider a pinhole model, the parameter that has the most influence on errors is focal length, and, to a lesser extent for present-day cameras, the position of the optical center and radial distortions. During image capture, practical generation errors, which influence the values of and confidence in these parameters, may arise and combine with one another, but also with imprecision in image digitization parameters: resolution, quality and dynamic range (compensations, etc.) of the sensor, compression of the image, etc.

Figure 1:
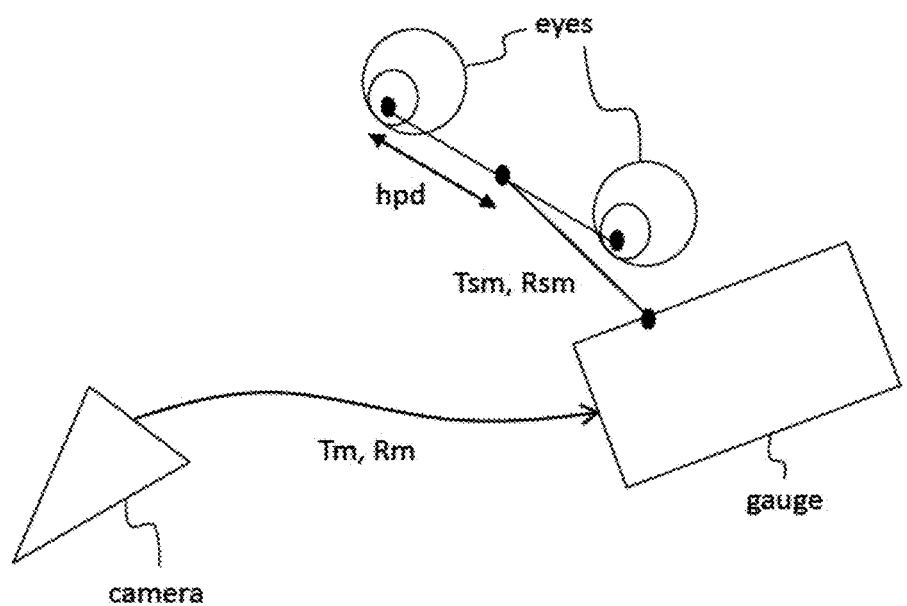
FIG. 1: a schematic representation of parameters taken into account in the measurement.

As regards parameters relating to the camera model and to the scene, and for 2D scaling in the image plane, between a gauge of known size and the quantity to be measured (the distance between the centers of the pupils), the following configurations are noteworthy:

Relationship of the Rigid User/Gauge (Denoted UG Below) System Relative to the Camera (see FIG. 1)

Position:

Distance: the closer the user/gauge (UG) system gets to the camera, the less distance relationships between visible points of the gauge and of the face of the user are preserved between the image and the 3D scene. These relationships and points of the 3D user/gauge UG system may even disappear from the image depending on the distance to the camera—for example the ears may disappear from the field of view if the user gets very close to the camera. The further the user/gauge UG system gets from the camera, the better the image scene is modeled by an orthographic projection model, i.e. the more closely the measurement relationships visible in the image match those of the actual scene. This is true for all the points that are not located in a plane fronto-parallel to the image plane of the camera.

Position in the image: the more closely the user/gauge UG system is aligned with the optical axis, and therefore centered in the image for most cameras, the smaller the error in the measurement. If the plane of the gauge and the plane of the measurement to be carried out (interpupillary distance) are coincident, the scaling may include an offset if the quantities to be measured are not centered. When scaling is carried out for a horizontal quantity and the subject is well centered in the image, then the distance scaling error is centered and depends only on the distance between the measurement and reference planes if these planes are fronto-parallel to the camera.

Thus, to carry out a scaling operation, the user/gauge UG system must be located far from the camera called low perspective, close to an orthographic view) and in the center of the image. The UG system must also be symmetric and centered between the quantities to be measured (distance between the eyes) and the reference quantities (gauge object) according to the dimensions necessary to the measurement.

Orientation: in the case where the system is oriented relative to the camera (face turned towards the right or left, or upward or downward), it is possible to carry out what would be called a satisfactory scaling operation only in the case where the reference quantity and the one-dimensional quantity to be measured are in the same plane, centered, of comparable size and of small orientation. If not, in theory (see for example: "Multiple View Geometry"), projective transformations preserve only cross ratio; a particular relationship between 8 points of the scene is required in order to make it possible to carry out the scaling. This configuration is possible and amounts to a 3D metric interpretation. In contrast, for 2D scaling of the image, errors will very rapidly increase with orientation, in proportion to how rapidly the quantities to be measured are decentered.

Camera/Gauge Object Relationship

The conclusions are here the same as above.

Face/Gauge Object Relationship

Depth position: if the gauge object is in the same plane as the quantity to be measured, then scaling may be carried out. If the planes are shifted depthwise relative to the camera, the scaling error generated will depend on the relationship between the camera distance and the user/gauge distance. The further the user/gauge UG pair is from the camera, the smaller the scaling error due to the depthwise shift. The closer the user/gauge UG pair, the larger the measurement error with regard to the expected precision.

Position and separation: the further the gauge object is from the eyes, the larger the error in the scaling. Specifically, parallax errors due to the position in the image arise in the measurement of each entity and corrupt the ratio between the gauge objects and eyes. If the face is considered to be located at the center of the image along a vertical axis of symmetry passing through the nose, then the gauge should also be positioned such that the measurement is distributed evenly on either side of the projection of the optical center in the image, in order to limit parallax errors intrinsic to the position of the gauge and, relatively, to the quantity to be measured on the face.

Orientation: orientation also gives rise to the parallax problem seen above.

Shape of the object: the object must be small (about 10 cm in size) and flat, in order to remain as stably as possible on the mouth and chin, or on the forehead. Gauge objects that are too large, heavy or thick would not allow such stability to be achieved. A smartphone displaying a planar image may be used, but its weight is higher relative to a credit card or compact disc (CD) and provides less positional comfort.

Rigid contact: if the gauge object does not make rigid contact with the face, it is not possible to guarantee the scaling. The protocol under which this object is held in a plane of the same depth as that of the eyes is subject to parallax errors, and in practice provides no guarantee that there will not be a small depthwise shift between the planes. Users in general make a centering error of about one centimeter, this being too imprecise to achieve the measurement quality desired for the scaling. The contact must be a flat contact, i.e. the gauge object must have at least 3 unaligned points of contact, in order to ensure the stability of the positioning. The solution that consists, in the case of the preceding protocol, in bringing the edge of a credit card into contact level with the eyes requires the head to be rotated and knowledge of the calibration in order to determine from a plurality of images the position and orientation of the gauge object.

All of these constraints favor the use of a gauge of limited size, positioned around the quantity to be measured. The ideal gauge is a pair of spectacles of known face-on size, and known eye-face distance. This gauge allows an ideal positional placement to be achieved, and helps obtain a face-on orientation via symmetric projection of the visible surface of the temples in the image. Another type of gauge that meets the bill is a credit card or CD, which is preferably placed in the mouth-chin zone or on the forehead.

User/Camera/Point to be Fixated Relationship

The system of the irises is not rigid. The centers of the eyeballs are considered to be the eye rotation centers. Iris and pupil are visible from the camera.

Fixation: during conventional measurement protocols carried out at an opticians, the user looks to infinity in order to measure the interpupillary distance measurement for an infinity-convergence. The user is considered to be looking to infinity when he is looking at a point located further away than a threshold distance 'ds' (generally one meter, but it may be as small as 70 cm and as large as infinity), in the context of scaling of an image.

The following are the two protocols that are possible in the context of our system:
  1. The user must fixate on a point located behind the camera at more than the threshold distance ds.
  2. The user must be located at more than the threshold distance ds and look at the camera or a point nearby.

Convergence: the precision of the vision of the user and his ability to converge his eyes on the point to be fixated may vary. In the general case, the user having a problem with his sight, his capacity to correctly fixate is limited. The fact that he is at a little less than one meter from the point to be fixated does not alter the precision of the measurement. For a user who can see well, his ability to adequately converge his eyes will mean that he will have to remain far away in order to meet the conditions for convergence at infinity, which allow the 2D measurement to be achieved.

The further the user is from the camera, the smaller the convergence or fixation error will be.

Precision of the Image and Measurement Indices

Another source of error is the precision of the image. In order to make it possible to carry out scaling, it is necessary to identify reference points in the image obtained, which reference points allow the scaling to be carried out. In general, proposed systems require a known length to be specified for the gauge object and the center of the pupils to be specified for the eyes. The problem then encountered and not treated by existing systems is the error made when designating and identifying these reference points, which is most often done by a human, or a recognition algorithm, but the imprecision of which is such that it is a source of more substantial error than the parallax error described above for conventional sensors.

On one hand, the system for digitizing the actual scene to generate the final digital image adds a number of conventional processing operations inherent to mass-market digital sensors: quantization, compression [etc.]. Sensor quality is increasing with time, but the quality of the image is not always good because of the combination of a plurality of known factors such as: the sensitivity of the sensor; light conditions; and hardware-dependent digital data transfer time, which generates size and compression constraints. The final image is often noisy, saturated or lacking in dynamic range, thereby limiting the precision with which the reference points may be located. Even if the sensor has a high resolution, compression algorithms introduce a great deal of imprecision into outlines or even hallucinate new ones. With an HD webcam sensor, the outline of a flat object may be several pixels wide.

On the other hand, identifying reference points that remain stable between images is difficult because of the imprecision in each image. Current systems let the user mark these reference points, who are not expert operators. Very large errors are made when designating the desired reference point. Since detecting algorithms are never 100% reliable, particularly for very noisy data, automatic systems may obtain errors as large as those obtained by an inexperienced human. Since the precision of the position of a reference point is altered both by its visibility and the designation operation itself, the errors add up and errors of as much as several pixels may result.

With the images of mass-market sensors, and under the constraints on the position of the user, these pixel errors represent several millimeters, thereby making the precision of the measurement of interpupillary distance unsatisfactory.

General Solutions Stemming from the Analysis. Protocol and Tools for Guaranteeing Constraints are Met We have deduced, from the preceding analysis, the optimal protocols depending on the type of mass-market sensor:

With a Single Image:
  Handheld camera: with good sensors, such as those of handheld cameras, the ideal protocol is for the user to position himself facing and at most two meters away. The protocol then requires either two people (one to take the photo) or an automatic trigger. In practice, the position and orientation of the UG system are not guaranteed: it is necessary for the two people to be the same height to prevent parallax errors due to their positions, and to obtain an image in which the orientation of the face is small. It is therefore necessary to align the respective positions and orientations of the UG and camera systems. One possible protocol is for the two people to be seated on chairs (in order to limit their height difference) at the largest possible distance at which the user can still see the objective. 2 meters is enough in practice. Alignment of the orientations of the UG and camera systems may be achieved with the user-position recommendations proposed in this patent. As the image capturing system does not have a screen, the positional indications are not related by software but by the person taking the photo.
  Webcam: webcams, whether they are integrated or not, are generally positioned above a screen. Even for high-quality sensors, image compression often has a substantial effect, as does image processing—which modifies outlines—and adjustment of brightness, white balance and other parameters, which are often automatically adapted to great effect. These effects alter the perceived position of the reference points. The webcam automatically adjusts to a neutral light. The user sits facing the camera. The program that controls the camera takes the photo automatically. Since the user must be as far away as possible, it is necessary to find the best compromise between size in the image, which must be maximal, and distance to the camera. The user should place himself at about arms length, between 70 cm and 1 m. The program displays in real-time the image of the acquired stream on the screen, and the image is magnified and contains an oval guide in its center such that the user places himself therein. Thus, centering and positional constraints are met.

A guide indicating the visibility of both ears is displayed for left-right angle of orientation, and a guide for horizontal alignment of the eyes with the axis of the tops of the ears (locations where spectacle temples rest) is displayed for up-down orientation.

One variant to the display of a guide is to implement a 3D facial tracking system that allows the optimal photo (best 3D pose of the face) to be taken with real-time feedback on the orientation of the face of the user.

Mobile sensor (smartphone, tablet): the same guides are displayed by virtue of a web program or an application. The user may by himself capture an image of himself with a front camera that returns him his image, as in the case of the webcam, or may be assisted by someone who follows the guides in order to ensure the user correctly fixates and that the protocol is carried out correctly, as in the case of the handheld camera. The case where the user captures an image of himself by himself is likely to lead to errors carrying out the protocol, because all the constraints that we have disclosed are not guaranteed to be met.

The variant described above also applies to this case.

In the 3 cases described, a possible variant to the use of a flat gauge is the use of a metric 3D model of the face (or some of the face) of the user (it is possible to scan his face beforehand, or to upload his 3D model into the application). After 2D points of the face, which are derived from the image, have been matched to their corresponding points of the metric 3D model, the gauge will then consist of at least 2 particular 3D points of the 3D facial model. Depending on the density of the 3D mesh of the face of the user, the model will also possibly be used in the facial tracking proposed in the above variant. In summary, knowledge of the metric 3D face of the user makes it possible to carry out facial tracking and the scaling using reference points on the 3D face.

Position and orientation of the UG system

Starting with a few images that are small in number (fewer than five), the eyes are assumed to be looking at a point at infinity and the direction of the gaze is assumed to be aligned with that of the UG system, i.e. the gaze is assumed to be directed almost perpendicular to the plane of the flat gauge. If the eyes were assumed to move and track a point independently of the orientation of the face, then this would amount to the case in the above patent FR 10 52001, and calibrated 3D resolution would be required. The case for which the orientation of the camera and the UG system are not aligned is examined.

CASE 1: system of the eyes in the same plane as the gauge plane, one point of view.

If the system of the eyes is assumed to be in the same plane or a plane nearby that of the gauge, then, for a flat gauge, it is possible to define a homographic relationship between a metric reference space and the image. This relationship may be written:
$xref\_i = H * x\_i$, where $x\_i$ are homogenous points in P3, a three-dimensional projective space.

It is then possible instead of carrying out the scaling directly on the image between the points $x\_i$, to carry it out in a normalized image space that guarantees preservation of distances, between the points $xref\_i$, which points are defined as images of the $x\_i$ and generated by a projective transformation H. This corrected measurement may be implemented with a single image or a plurality of images with different UG orientations and positions.

This approach allows errors in the precision of the marking of the points of interest in the images to be minimized.

CASE 2: system of the eyes in different planes than that of the gauge, one point of view It is not possible to carry out reliable scaling in this general case from a single image, except in the case where the orientation is small and the distance between the UG and the camera is large, in which case the errors are negligible on the scale of the measurement.

With a Plurality of Images:

1/ If the camera is not calibrated, the scenarios described above may be applied to a plurality of images, thereby making it possible to make the measurement robust by way of statistical analysis of the measurements (such as mean or standard deviation for example).

2/ The camera moves and the user looks at a point at infinity without moving. The user taking the image needs to make only a small movement. The gauge must be visible throughout the movement and positioned rigidly relative to the face. From a large number of acquired images (two in theory), or a video, it is possible to reconstruct in 3D, using conventional techniques, the rigid UG system metrically in the case where the camera is calibrated.

One variant is to replace the flat gauge with the use of a metric 3D model of the face (or some of the face) of the user (it is possible to scan his face beforehand, or to upload his 3D model into the application).

If the camera is not calibrated, it is not possible to estimate the metric relationship between the gauge and the eyes, and it is then necessary to define it (same plane or not, rigid 3D relationship, etc.). The practical problem that then arises is that of the digital precision of this relationship (which depends on image resolution, on distance and on the size of the gauge object) relative to the precision required for the measurement to be carried out. In general, for a precision of about 0.5 millimeters for the interpupillary distance, the precision required for the relationship to be defined between the camera and the eyes CY is of the same order, which in practice is impossible to obtain.

Let us take the example where the size and 3D morphology of the face of the user is known; the face is, for the eyes, the best gauge that it is possible to obtain. If it is desired to measure the distance between the centers of the pupils, then it is necessary to determine the relationship of the depth of the plane of the pupils relative to this face, and an error of about half a millimeter introduces an imprecision of the same order.

Lastly, even when the camera is not calibrated, the resolution obtained with the homographic relationship and a single image is satisfactory, since it allows the scaling to be carried out in a normalized space. The 3D approach described here however introduces stability into the measurement, since the number of images and the orientation of the user who takes them with the camera allows statistical methods to be applied to the measurement, and thus an equation characterizing the error made to be obtained.

One way of proceeding is to reconstruct the eyes/gauge system in the following way (see FIG. 1):

A/ firstly find the transformation (translation, rotation) undergone by all of the points of the gauge in each acquired image.

For each image, point-difference minimization is carried out (minimization conventionally solved by Gauss-Newton algorithms).

We are seeking to minimize the following expression:

$$\operatorname{argmin}_{Rm,Tm} \sum_{i=1}^{nPts} [P_{2D}(i) - Proj(Dp(P_{3D}(i), Rm, Tm)]^2$$

where

Rm, 3D rotation matrix between the camera and gauge;
Tm, 3D translation vector between the camera and gauge;
nPts, number of projected points;
$P_{3D}$, 3D coordinates of the gauge;
$P_{2D}$, 2D coordinates of the gauge in the image (corners, outline points, characteristic points);
Proj, function projecting a 3D point into the image (pinhole model for example)

$$Proj(P_{3D}) = \begin{bmatrix} x/z \\ y/z \end{bmatrix} \text{ where }$$

$$\begin{bmatrix} x \\ y \\ z \end{bmatrix} = KM * P_{3D}$$

and KM, calibration matrix of the camera (precisions in the calibration menu)

$$KM = \begin{bmatrix} f & 0 & u0 \\ 0 & f & v0 \\ 0 & 0 & 1 \end{bmatrix}$$

$D_p$, being the function applying the rotation matrix R and the translation vector T to a 3D point for a movement in 3D $$D_p(P_{3D}) = R*P_{3D}+T.$$

B/ Then find the value of each variable $T_{SM}$, $R_{SM}$ and hpd that are common to all the acquired images Where:
hpd, distance between the center of the system of the eyes and the center of each pupil;
Rsm, rigid 3D rotation matrix between the gauge and the system of the eyes; and
Tsm, rigid 3D translation vector between the gauge and the system of the eyes.

In all the images, a point-difference minimization is carried out $$\operatorname{argmin}_{hpd, Rsm, Tsm}$$

$$\sum_{i=1}^{nPts} \sum_{j=1}^{nlm} [P'_{2D}(i, j) - Proj(Dp(Dp(P'_{3D}(i, hpd), Rsm, Tsm), Rm(j), Tm(j))]^2$$

Where:
Rm, 3D rotation matrix of the gauge (per image);
Tm, 3D translation vector of the gauge (per image);
nPts, number of projected points;
nlm, number of acquired images;
$P'_{3D}$, 3D coordinates of the pupils;
$P'_{2D}$, 2D coordinates of the pupils in the image;
Proj, function projecting a 3D point into the image (pinhole model for example); and
$D_p$, function applying a rotation matrix R and a translation vector T to a 3D point for a movement in 3D.

3/ The camera remains stationary and the user moves while looking at a point at infinity. The gauge must be visible throughout the movement and positioned rigidly relative to the face. From a large number of acquired images (two in theory), or a video, it is possible to reconstruct in 3D, using conventional techniques, the rigid UG system metrically in the case where the camera is calibrated.

One variant is to replace the flat gauge with the use of a metric 3D model of the face of the user.

4/ The camera is calibrated and remains stationary and the user moves while looking at a plurality of points on a screen/plane.

One variant is to replace the flat gauge with the use of a metric 3D model of the face of the user.

5/ The camera is calibrated and moves and the user remains stationary while looking at a plurality of points on a screen/plane.

One variant is to replace the flat gauge with the use of a metric 3D model of the face of the user.

6/ The camera is not calibrated and generates a depth map (camera such as the Kinect®). A more precise scaling may be achieved in this case since the user-camera and camera-gauge distances are known. These distances are more simply estimated as in the protocols with a single image.

7/ The camera is calibrated and generates a depth map (camera such as the Kinect®). In this case a gauge is not required. Since the calibration of the camera and the depth of the face in the scene are known, the distance between the pupils is deduced directly therefrom.

Proposed Solution for Simple Scaling with a Precision of <0.5 mm for a Mass-Market Sensor Without Calibration Architecture of the System:
a camera: webcam, handheld camera, tablet, depth-map camera;
a processor, a screen;
a precise protocol for user/gauge/camera (UGC) positioning;
a set of interactive recommendations that allow this positioning to be achieved without error;
a tool for marking, following recommendations, the reference points;
a corrected, measurement scaling calculation.

Gauges with the following properties:
sufficiently large contact area to ensure stability on the face;
around the eyes, or as close as possible: centered on and near the elements that it is desired to measure; and
objects that have a certain symmetry for easy positioning.

Examples of gauges:
- spectacles of known size and eye-face distance (in general 15 mm);
- a credit card;
- a CD; and
- a face of known dimensions, or of measured constituent elements (such as the corners of the eyes).

Protocol and Indications Given when Carrying it Out

The subject must place himself at a known (or estimatable) distance from the image acquiring device and look straight ahead (at a particular point or at the acquiring device for example) while placing a rigid object of known size (gauge) at a known (or estimatable) distance from the plane containing his pupils. It will be recalled that in the case where the metric 3D face of the user is known, the gauge plane is not necessary.

An image of the subject is then acquired when his head is straight in front of the camera (eyes and ears almost aligned). Ideally, the 2 ears of the subject must be visible equivalently. A video stream may be recorded while the user makes a particular movement of his head, allowing the most appropriate image to be chosen. The image may also be chosen automatically by virtue of 3D tracking of the face.

The rigid object is ideally placed at a set or (statistically) estimatable distance from the plane containing the pupils; a face of the gauge object must be as parallel as possible to this plane containing the pupils. For example, the rigid object may be placed on the forehead, on a cheek or the mouth of the user.

The indications given in practice are as follows, in the case where the gauge is a credit card:
1. The user positions himself seated in front of his screen, at an outstretched arm's length from the camera, which is assumed to be located centered on top of the screen. He must be able to see his face centered on the screen.
2. If he is wearing spectacles, he removes them. For most corrections, our protocol allows the quality of the measurement to be guaranteed without need for spectacle removal.
3. He positions the card on his mouth, taking care to exert enough pressure with his index finger that the card remains fixed and meets the condition of planar stability.
4. The user then adjusts the orientation of his head taking care:
   a. Heightwise: that the horizontal line passing through his pupils, or the corners of his eyes, is at the same height in the image as the points where his ears start on his temples, i.e. the points on which the temples of a pair of spectacles would rest.
   b. Widthwise: to guarantee that he, the user, is able to see the left- and right-hand portions of his face symmetrically, by virtue of indices. Positionwise, this was discussed in point 1. Orientationwise, this guarantee is achieved by indicating to the user reference points in the image that guarantee a face-on orientation for which the head is turned neither too much to the left nor too much to the right. For example, both ears must be visible. Since the ears are in a plane that is at least 10 cm behind the eyes, any, even small, angle of the head leads to a substantial movement of these objects in the image, and to the head blocking the line of sight thereto from the point of view of the camera. The ears very rapidly disappear if the head is not directionally aligned with the line of sight of the camera.
5. The user looks at the camera.
6. The software package takes the photo.

One variant:
1. The user positions himself seated in front of his screen, at an outstretched arm's length from the camera, which is assumed to be located centered on top of the screen. He must be able to see his face centered on the screen.
2. If the user is wearing spectacles, he removes them. The user holds the card ready.
3. 3D facial detection and tracking.
4. The facial tracking helps the user to correctly position his face.
5. The user places the card on his mouth and looks at the camera.
6. The software package takes the photo.

Another variant (in the case where the metric face of the user is known):
1. The user positions himself seated in front of his screen, at an outstretched arm's length from the camera, which is assumed to be located centered on top of the screen. He must be able to see his face centered on the screen.
2. If he is wearing spectacles, he removes them.
3. Metric 3D facial detection and tracking.
4. The facial tracking helps the user to correctly position his face.
5. The user looks at the camera.
6. The software package takes the photo.

The interactive feedback and indications given are as follows:
1. Positioning: positioning imagery. A symmetric (rectangular, oval, etc.) guide is displayed centered in the image and the size of which depends on the resolution of the camera and on an assumed focal length. This frame allows the user to validate his position, movement- and depthwise, relative to the camera. Vertical or horizontal lines may be added in order to help with heightwise positioning of the eyes or the horizontal symmetry of the face.
2. An indication to remove spectacles.
3. One or more positional examples.
4. Optional guides for the image capture:
   a. Heightwise: a series of 3 horizontal parallel lines indicating the line on which the eyes should be positioned and the permissible variability thereabove or therebelow, corresponding to a vertical rotation of the head upward or downward, which allows the expected measurement precision to be obtained.
   b. Widthwise: visual indications as to visibility.

Calculation of the Scaling Between the Gauge and the Ocular Distance to be Measured The resolution of the measurement consists in carrying out scaling between the size of the gauge object and the size in pixels of the quantity to be measured in the acquired image. Specifically, assuming the gauge object and the quantity to be measured are in the same plane, the relationship between the number of pixels defining a quantity of the gauge object and its actual size serves as a reference for calculating D, the distance between:
- the centers of the pupils, in the case of calculation of PD.
- the center of one pupil and the bridge of the nose of the subject (or the center of the frame), in the case of calculation of monoPD.
- the bottom of the frame of a pair of spectacles and the center of a pupil, in the case of calculation of pupillary height.

Figure 2:
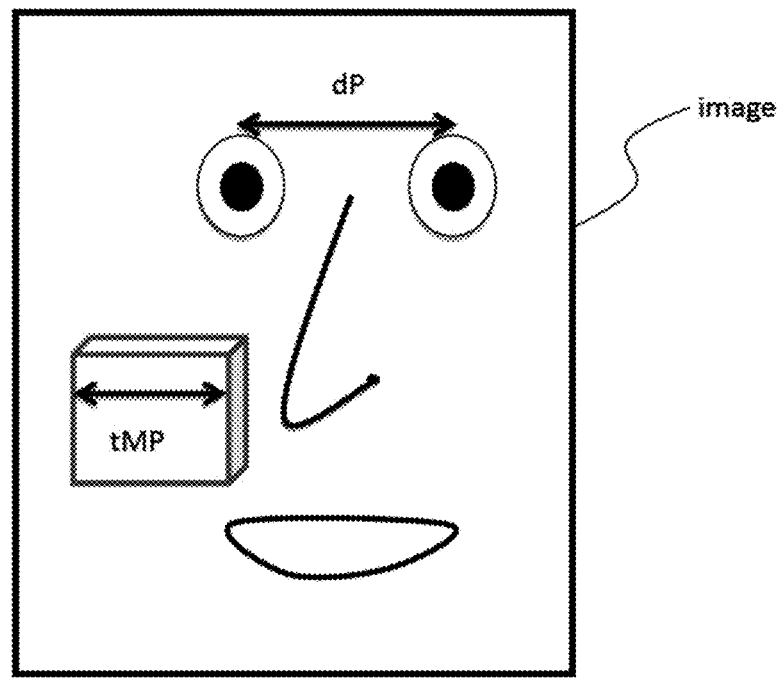
FIG. 2: a schematic view of an image obtained by the camera.

The measurement D in mm is then estimated by $D = dP \cdot tMM/tMP$. Where dP is the distance D expressed in pixels (in the image), tMM is the measurable quantity of the rigid object (gauge) in millimeters and tMP is the size of the gauge in pixels in the acquired image (see FIG. 1 and FIG. 2).

Figure 3:
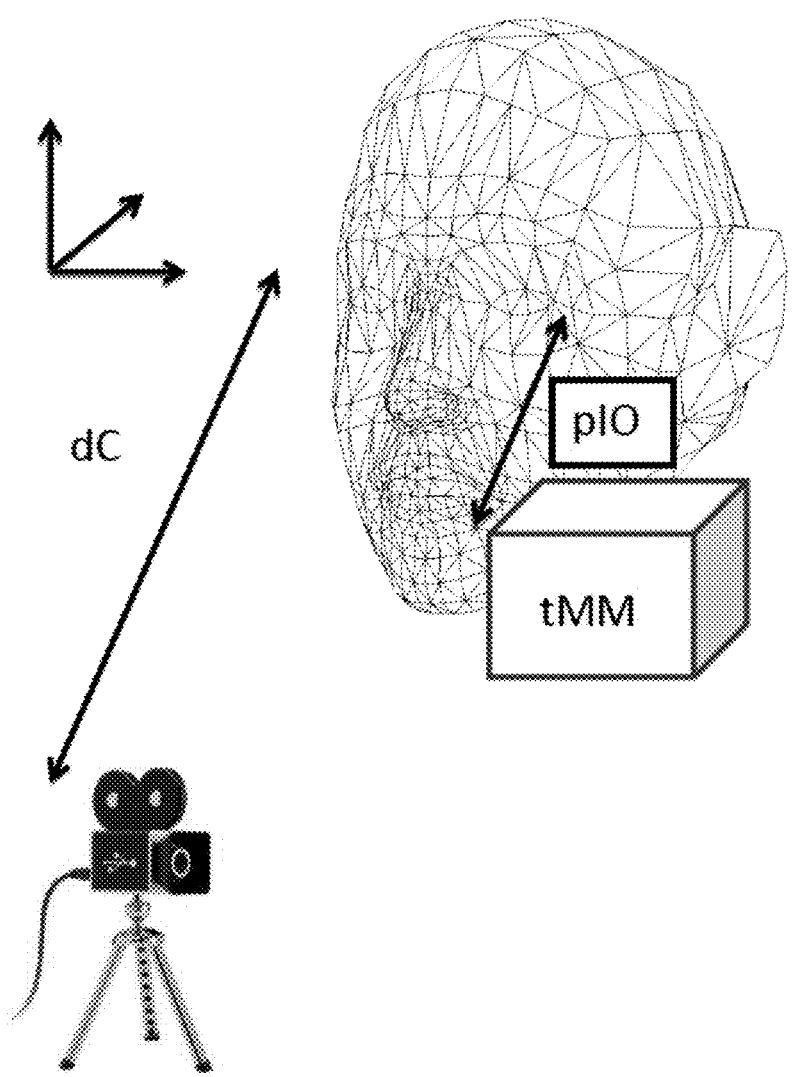
FIG. 3: a diagram of elements involved in the taking of measurements.

For greater precision, enhancive corrections may be made:

If the focal distance (fe) of the acquiring device is unknown, it may be estimated by fe=dC*tMP/tMM. Where dC is the (known, estimated or assumed) distance between the subject and the acquiring device in millimeters (see FIG. 3).

The size of the gauge in pixels in the acquired image may then be corrected (the corrected value is denoted tMP2); it is a question of an estimation of the size that the gauge object would have if it were located in the plane of the pupils (in the case of calculation of PD and monoPD) or of the lenses (in the case of calculation of pupillary heights):

tMP2=tMP*fe/(dC+plO). Where plO is the (known, estimated or assumed) depth between the plane containing the known quantity of the rigid object (gauge) and the plane containing the pupils (in the case of calculation of PD and monoPD) or the lenses (in the case of calculation of pupillary heights).

The corrected measurement D is equal to: dP*tMM/tMP2.

Lastly, if the distance dC is smaller than 60 cm and the subject is looking no further away than 1 m, a correction may be added to convert this near-vision pupillary distance to a far-vision distance.

In practice, a software package allowing the image capture and the calculations to be carried out may take the form of an application and/or an Internet site/plug-in for a web browser. This software package may guide the user as to the placement of his camera and to the positioning of his gaze.

In the case where the calibration of the camera is known, it is obvious that the estimation of the focal length (fe) is no longer necessary, and the precision of the measurement is therefore higher.

Processing Tool Ensuring the Precision of the Image Indices

In order to allow a high precision to be obtained when marking the indices, we propose a suitable interface. This interface may be used by the final user, but above all is provided to be used by a trained expert in order to assure process stability.

The expert uses this interface to:
1. identify orientational and positional errors;
2. choose the best photo according to criteria of protocol compliance quality, but also of visibility of the indices. The expert may reject photos the quality of which is too low for the indices to be identified, or that attest to insufficient protocol compliance. The architecture of the system then makes it possible to contact the user again, so that he can be asked to capture an additional image under better conditions; and
3. mark the image indices that allow the measurement.

Claimed Functionalities of the Interface

In order to guarantee the maximum precision during placement of the reference points, the interface guarantees at any moment and in the same display field of view:
1. an overall view of the scene;
2. a magnified local view of the portion of the image in which the index is to be marked; and
3. positional indications and guides for difficult cases.

These coupled views allow the expert user to be precise and perfect his marking technique.

When the image on which reference points are to be marked is presented, the interesting portions of said image may already be magnified in the overall view, by virtue of the controlled positioning of the user during the protocol.

Marking of Eye Reference Points

In order to mark the centers of the eyes, we propose the placement of a circle equipped with targeting lines pointing toward the center of the circle on the iris by the expert user. The placement must be carried out such that the curvature of the circle follows that of the iris at equal Euclidean distance at each point. During this placement, the magnified portion of the interface makes it possible to be very precise.

Marking of Gauge Reference Points

For a credit card, the interface proposes an overall and local approach to handling of the reference shape. A rectangle is presented to the user, of size and positions similar to those expected in the image. This rectangle possesses four control points. An overall deformation mode allows scale- and rotationwise deformation to be controlled, with a set width/height ratio. Normally, a card well positioned when carrying out the protocol should have an image that allows the geometric model of the interface to be aligned with the image.

The magnified portion of the interface allows local uncertainty due to image compression and quantization problems to be managed. The second mode of modification of the geometric shape of the card allows the position of the points to be modified one by one and independently of the others. Since these points are connected together, the expert user may see the line formed between these points and thus follow the silhouette of the card exactly. The geometric shape thus closely follows the outlines of the projective deformation of the image of the actual card. If this deformation is too large, this gives an indication of protocol compliance quality. Often, problems due to unsuitable quantization and image compression arise in zones of low contrast. Thus, the outline may no longer be visible all the way around the card. The expert user may then choose the most relevant zones to use. A black strip being present on the back of the card, the contrast may be high level therewith, and the geometric rectangle may be fitted to this strip if necessary.

The marking is carried out with local-scale precision compensated by overall-scale coherence. Lastly, learning algorithms may be implemented in order to guarantee these constraints during adjustment of the geometric model in the example image (outline, texture, etc.).

The distance used for the measurement is the distance located at the top of the strip, which corresponds to the most stable points of contact of the card against the face, and for which the hypotheses made as regards the scaling are the most reliable.

For any other flat object, care will be taken to make allowance for the possibility of projective deformations in the silhouette of the object in question, in order to obtain the tightest possible fit to its silhouette in the image. Thus, for a CD, a double circle that it will be possible to convert into an ellipse will be adjusted.

This marking operation is valid both for the protocol when the person is face-on and oriented, and when a space normalized via homographic relationship is used.

Extensions

Calibrated multi-camera system: 3D reconstruction
1. Nothing moves, gaze to infinity.
2. The eyes look at a point that moves over a screen.

The method described here guarantees a successful measurement by virtue of:
a protocol that is easy to understand and carry out;
interactive guides; and an annotation tool that is easy to understand and use, which guarantees the precision of the annotation of the reference points required for the measurement.

The method eliminates detection and parallax errors and guarantees the right conditions and corrections for correct scaling.

The invention claimed is:

1. A method for determining at least one ocular measurement (interpupillary distance, monocular pupillary distance and/or pupillary heights) of a user from at least one image of the user's head acquired by a mass-market digital image sensor, the user seeing in real time said at least one image of his head displayed on a display screen, the method comprises steps of:
   determining a tridimensional orientation of the face of the user compared to the image sensor by a face tracking system executed by a processor;
   displaying visual landmarks on said at least one image displayed on the display screen to guide the tridimensional orientation of the user's head compared to the image sensor in relation with a feedback provided by the face tracking system;
   determining said at least one ocular measurement by the processor on said at least one image from a measurement of an object comprised in the image by determining the tridimensional orientation of the object and by scaling between a size of the projected object and a pixel size of said at least one image, the object having a known size; and
   tracking a position and the tridimensional orientation of the user's face in real time, and determining the visual landmarks according to the position and the tridimensional orientation of the user's face at each instant.

2. The method as claimed in claim 1, wherein the object of known size is the face of the user.

3. The method as claimed in claim 1, wherein the object of known size is a flat object.

4. The method as claimed in claim 1, wherein the object of known size is a pair of spectacles.

5. The method as claimed in claim 4, wherein the user is at a known distance from the acquiring device and wherein the object of known size is positioned at a known distance from the ocular measurement.

6. The method as claimed in claim 4, wherein the user is guided by an interactive system for helping with correct positioning.

7. The method as claimed in claim 4, wherein the interactive system for helping with correct positioning is a shape drawn on the display screen.

8. The method as claimed in claim 4, wherein the interactive system for helping with correct positioning includes recommendations derived from real-time facial tracking.

9. The method as claimed in claim 1, wherein the head of the user is face-on in at least one image.

10. The method as claimed in claim 9, wherein the user is guided by an interactive system for helping with correct positioning.

11. The method as claimed in claim 9, wherein the interactive system for helping with correct positioning is a shape drawn on the display screen.

12. The method as claimed in claim 9, wherein the interactive system for helping with correct positioning includes recommendations derived from real-time facial tracking.

13. The method as claimed in claim 1, wherein the user is at a known distance from the digital image sensor and wherein the object of known size is positioned at a known distance from the ocular measurement.

14. The method as claimed in claim 13, wherein the interactive system for helping with correct positioning is a shape drawn on the display screen.

15. The method as claimed in claim 1, wherein the user is guided by an interactive system executed by the processor for helping with correct positioning.

16. The method as claimed in claim 1, wherein the interactive system for helping with correct positioning is a shape drawn on the display screen.

17. The method as claimed in claim 1, wherein the interactive system for helping with correct positioning includes recommendations derived from real-time facial tracking.

18. The method as claimed in claim 1, wherein the mass-market sensor is calibrated and acquires images while moving around the face of the user who looks at a point at infinity.

19. The method as claimed in claim 1, wherein the mass-market sensor is calibrated and acquires images while moving around the face of the user who looks at points displayed on the display screen.

20. The method as claimed in claim 1, wherein the mass-market sensor is calibrated and delivers a depth map of a scene.

* * * * *